United States Patent [19]
Takahashi et al.

[11] Patent Number: 5,380,723
[45] Date of Patent: Jan. 10, 1995

[54] INDOLE DERIVATIVES

[75] Inventors: Toshihiro Takahashi; Hitoshi Inoue, both of Saitama; Masato Horigome, Tokyo; Kenichi Momose, Saitama; Masanori Sugita, Saitama; Kouichi Katsuyama, Saitama; Chikako Suzuki, Saitama; Shinji Nagai, Saitama; Masao Nagase, Saitama; Koichi Nakamaru, Saitama, all of Japan

[73] Assignee: Nisshin Flour Milling Co., Ltd., Tokyo, Japan

[21] Appl. No.: 228,505

[22] Filed: Apr. 15, 1994

Related U.S. Application Data

[62] Division of Ser. No. 949,028, Sep. 22, 1992, Pat. No. 5,326,879.

[30] Foreign Application Priority Data

Oct. 7, 1991 [JP] Japan .................. 3-285535

[51] Int. Cl.$^6$ .............. A61K 31/44; A61K 31/445; A61K 31/47; A61K 31/40; C07D 401/14; C07D 403/14; C07D 413/14
[52] U.S. Cl. ................... 514/235.8; 514/310; 514/323; 514/339; 514/414; 546/273; 546/201; 546/165; 546/148; 544/143; 548/455
[58] Field of Search ............... 548/455; 546/165, 201, 546/273, 148; 514/310, 323, 339, 414; 544/143

[56] References Cited

FOREIGN PATENT DOCUMENTS

| | | |
|---|---|---|
| 0254223 | 1/1988 | European Pat. Off. . |
| 0512824A1 | 11/1992 | European Pat. Off. . |
| 52-102279 | 8/1977 | Japan . |
| 54-12375 | 1/1979 | Japan . |
| 54-90179 | 7/1979 | Japan . |
| 54-103871 | 8/1979 | Japan . |
| 54-125672 | 9/1979 | Japan . |
| 59-501950 | 11/1984 | Japan . |
| 63-27484 | 2/1988 | Japan . |
| 1565083 | 4/1980 | United Kingdom . |
| 84/01775 | 5/1984 | WIPO . |

OTHER PUBLICATIONS

Chain et al., "Pseudomonic Acid. Part 3. Structure of Pseudomonic Acid B", 1977, pp. 318–322, J. Chem. Soc. Perkin Trans, I.

Clayton et al., "The Chemistry of Pseudomonic Acid. Part 5. Structure and Chemistry of Pseudomonic Acid C. X-Ray Crystal Structure of Ethyl Monate C," 1982, pp. 2827–2833, J. Chem Soc. Perkin Trans. I.

O'Hanlon et al., "The Chemistry of Pseudomonic Acid. Part 6. Structure and Preparation of Pseudomonic Acid D", 1983, pp. 2655–2657, J. Chem. Soc. Perkin Trans. I.

Ettlinger et al., "Stoffwechselprodukte von Actinomyceten", 1959, pp. 563–569, Helv. Chim. Acta, 42.

(List continued on next page.)

Primary Examiner—David B. Springer
Attorney, Agent, or Firm—Abelman, Frayne & Schwab

[57] ABSTRACT

Disclosed are indole derivatives of formula (I)

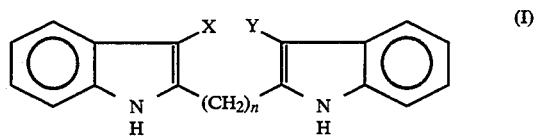

wherein X and Y each independently represent H or —CH$_2$CH$_2$R;

R represents pyridyl or substituted amino of NR$_1$R$_2$;
R$_1$ represents H or C$_1$–C$_6$ alkyl;
R$_2$ represents 2-(3-indolyl)ethyl or aralkyl; or
R$_1$ and R$_2$ together with the nitrogen atom to which they are attached may form an N-containing 5 to 6 membered hetero ring, an N, O-containing hetero ring, which hetero ring may be fused with benzene;
n is an integer of 4 to 8;

with the proviso that X and Y both do not represent H or piperizinoethyl when n is 4, or pharmaceuticaly acceptable acid addition salts thereof. They are useful as an antiulcer agent.

5 Claims, No Drawings

OTHER PUBLICATIONS

Celmer et al., "The structures of Thiolutin and Aureothricin, Antibiotics Containing a Unique Pyrrolinonodithiole Nucleus", 1955, pp. 2861–2865, J. Am. Chem. Soc., 77.

Angew. Chem., 66, 745, 1954.

Communications to the Editor, "Characterization of the Antibiotic Thiolutin and its Relationship with Aureothricin", 1952, pp. 6304–6305, J. Am Chem. Soc., 74.

Abstracts of Papers from the 200 Year Conference of the Am. Chem. Soc. (Aug. 26–31, 1990), Part 2, Orgn. No. 139.

Experimentia, vol. 48, pp. 1165–1169 1992.

McInerney et al., "Biologically Active Metabolites from Xenorhabdus Spp., Part 1. Dithiolopyrrolone Derivatives with Antibiotic Activity", 1991, pp. 774–784, Journal of Natural Products, 54.

INDOLE DERIVATIVES

This is a division of application Ser. No. 07/949,028 filed on Sep. 22, 1992, U.S. Pat. No. 5,326,879.

FIELD OF THE INVENTION

This invention relates to new indole derivatives and pharmaceutical compositions comprising them which are useful as antiulcer agents.

BACKGROUND OF THE INVENTION

Known medicaments which have been used as antiulcer agents include $H_2$-receptor antagonists representative of which is cimetidine, gastric acid secretion inhibitors such as omeprazole inhibiting proton pump ($H^+,K^+$-ATPase) and medicaments having gastric mucosa protection activity, which are chosen depending on the symptom of patients. However, those medicaments are of such disadvantages as generally weak activity and occurrence of side effects. For instance, cimetidine, representative of $H_2$-receptor antagonists have encountered the presence of intractable ulcer. Omeprazole has suffered from the occurrence of carcinoid and the interaction with other drugs including diazepam and phenytoin such as a lowering of hepatic clearance. Thus there is a continuing need for effective antiulcer agents.

The present invention results from efforts to develop new indole derivatives with more improved untiulcer effect.

DISCLOSURE OF THE INVENTION

According to the invention, there are provided indole derivatives of formula (I)

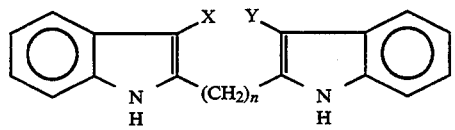

wherein X and Y each independently represent H or —$CH_2CH_2R$;

R represents pyridyl or substituted amino of $NR_1R_2$;
$R_1$ represents H or $C_1$-$C_6$ alkyl;
$R_2$ represents 2-(3-indolyl)ethyl or aralkyl; or
$R_1$ and $R_2$ together with the nitrogen atom to which they are attached may form an N-containing 5 to 6 membered hetero ring, an N, O-containing hetero ring, which hetero ring may be fused with benzene;
n is an integer of 4 to 8;
with the proviso that X and Y both do not represent H or piperizinoethyl when n is 4, or pharmaceuticaly acceptable acid addition salts thereof.

Suitable pharmaceutically acceptable acid addition salts of the compounds of formula (I) include acid addition salts formed with organic or inorganic acids such as hydrochlorides, hydrobromides, sulfates, phosphates, acetates, succinates, citrates, tartrates, fumarates and maleates.

In the definition of formula (I), $C_1$-$C_6$ alkyl represented by $R_1$ includes, for example, methyl, ethyl, n-propyl, isopropyl, n-butyl, isobutyl and n-hexyl. Aralkyl represented by $R_2$ includes e.g., benzyl, phenylethyl, phenylpropyl and phenylbutyl. When $R_1$ and $R_2$ together with the nitrogen atom to which they are attached form an N-containing 5 to 6 membered hereto ring or an N, O-containing hetero ring, the 5 to 6 membered hetero ring includes e.g., pyrrolidine and piperidine and the N, O-containing hereto ring includes e.g., morpholine. When those hetero rings are fused with benzene, the fused ring includes e.g.,

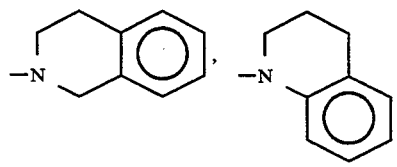

Representative compounds of formula (I) are listed below.

3,3-Di(2-piperidinoethyl)-2,2'-hexamethylenediindole,
3-(2-Piperidinoethyl) -2,2'-hexamethylenediindole,
3-(2-Phenethylaminoethyl)-2,2'-tetramethylenediindole,
3-(2-Piperidinoethyl)-2,2'-octamethylenediindole,
3-(2-Morpholinoethyl)-2,2'-tetramethylenediindole,
3-(2-Piperidinoethyl)-2,2'-tetramethylenediindole,
3,3'-Di(2-benzylaminoethyl)-2,2'-tetramethylenediindole,
3-(2-Benzylaminoethyl)-2,2'-tetramethylenediindole,
3,3'-Di(2-(1,2,3,4-tetrahydroisoquinolin-2-yl)ethyl)-2,2'-tetramethylenediindole,
3-(2-(1,2,3,4-Tetrahydroisoquinolin-2-yl)ethyl)-2,2'-tetramethylenediindole,
3,3'-Di (2-pyrrolidinoethyl)-2,2'-tetramethylenediindole,
3-(2-Piperidinoethyl)-2,2'-tetramethylenediindole,
3,3'-Di(2-phenethylaminoethyl)-2,2'-tetramethylenediindole,
3,3'-Di (2-(1,2,3,4-tetrahydroquinolin-1-yl)ethyl)-2,2'-tetramethylenediindole,
3-(2-(1,2,3,4-Tetrahydroquinolin-1-yl)ethyl)-2,2'-tetramethylenediindole,
3-(2-(2-(3-Indolyl)ethylamino)ethyl)-2,2'-tetramethylenediindole,
3,3'-Di(2-(N-methylbenzylamino)ethyl)-2,2'-tetramethylenediindole,
3-(2-(N-Methylbenzylamino)ethyl)-2,2'-tetramethylenediindole,
3,3'-Di(2-(3-phenylpropylamino)ethyl)-2,2'-tetramethylenediindole,
3-(2-(3-Phenylpropylamino)ethyl)-2,2'-tetramethylenediindole,
3,3'-Di(2-(4-phenylbutylamino)ethyl)-2,2'-tetramethylenediindole,
3-(2-(4-Phenylbutylamino)ethyl)-2,2'-tetramethylenediindole,
3,3'-Di(2-(2-pyridyl)ethyl)-2,2'-tetramethylenediindole.

The compounds of formula (I) can be prepared in accordance with known methods as shown in Scheme I, for instance using the methods mentioned in M. Julia et al. Bull. Chim. Soc. France, 1953–1956 (1964) or Sakai et al. Yakugaku Zasshi 95, 1152–1160 (1975).

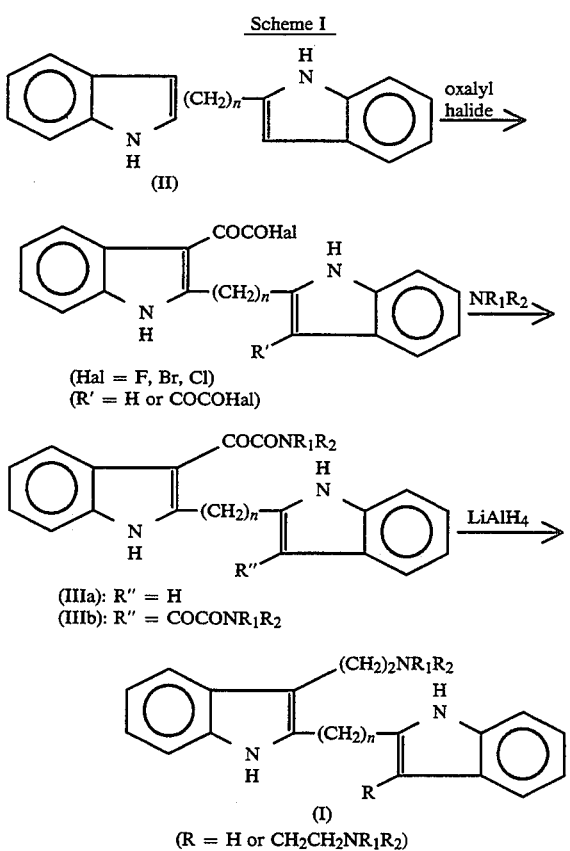

(R = H or CH$_2$CH$_2$NR$_1$R$_2$)

The starting bisindole compound of formula (II) is reacted with an oxalyl halide, e.g., oxalyl chloride in an inert solvent such as ether, tetrahydrofuran or the like. After isolation or without isolation of the reaction product, it is reacted with an amine to prepare a glyoxylamide of formula (IIIb). The reaction is usually carried out at a temperature in the range of 0° C. to room temperature. In that case, the compound of formula (IIIa) wherein only once of the indoles rings is substituted can be produced by controlling the amount of oxalyl halides used. A preferred amount of the halides used is 1 to 2 equivalents. Subsequently, the amide of formula (III) is reduced with lithium aluminum hydride to give the corresponding amine of formula (I).

Alternatively, the compound of formula (I) wherein R is pyridyl can be prepared in accordance with a known method (A. P. Gray et al. JACS 79 (1957) 3554), for instance by reacting the starting bisindole compound with the corresponding vinylpyridine in acetic acid. A preferred reaction temperature is from room temperature to a reflux temperature of the solvent used.

The compounds of formula (I) and their pharmaceutically acceptable salts exert an anti-secretory effect by inhibition of H+/K+ATPase and are useful as an antiulcer agent.

Thus the invention also provides a pharmaceutical composition which comprises as an active ingredient an effective amount of the compounds of formula (I) or pharmaceutically acceptable acid addition salts thereof. Such compositions may be formulated in conventional manner using one or more pharmaceutically acceptable carriers and/or excipients.

The compounds of formula (I) and their pharmaceutically acceptable salts inhibit exogenously and endogenously stimulated gastric acid secretion and are useful as an antiulcer agent in the treatment of gastrointestinal diseases such as gastric and duodenal ulcers, gastritis, reflux esophagitis and Zollinger-Ellison Syndrome.

The compounds of the invention can usually be administered orally or parenterally in the form of various pharmaceutical preparations. For oral administration, the pharmaceutical compositions may take the form of solid preparations including tablets such as sugar-coated tablets, capsules such as soft and hard capsules and liquid preparations such as solutions, emulsions or suspensions. For parenteral administration, the compositions may take the form of injections. Such solid preparations can be prepared by conventional means with pharmaceutically acceptable excipients such as binding agents, fillers, lubricants, disintegrants or wetting agents. Such liquid preparations can be prepared by conventional means with pharmaceutically acceptable additives such as suspending agents, emulsifying agents, non-aqueous vehicles and preservatives. The preparations may also contain buffer salts, flavoring, coloring and sweetening agents if desired.

The active ingredient is contained in the formulation in an amount of 0.1–100% by weight, suitably 1–50% by weight in the case of formulations for oral administration and 0.2–20% by weight in the case of formulations for injection based on the weight of the formulation.

Route and dosage of administration for the compounds of the invention are not specifically limited and are appropriately chosen depending upon form of the formulation, age and sex of the patient, severity of the disease and other factors. Daily dosage of the active ingredient is 1 mg to 2000 mg.

The invention is further illustrated by the following non-limitative examples.

EXAMPLE 1

3,3'-Di(2-piperidinoethyl)-2,2'-hexamethylenediindole

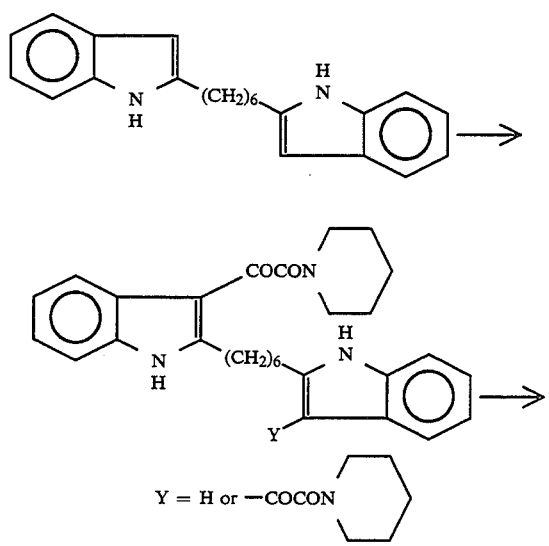

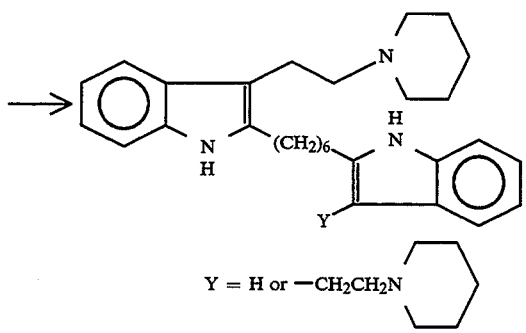

Y = H or —CH₂CH₂N⟨piperidine⟩

(1) Hexamethylene-2,2′-bisindole (3.21 g) was added to anhydrous ether. Oxalyl chloride (1.8 ml) was added dropwise under ice-cooling and stirring was continued for 2 hrs. Then piperidine (5.0 ml) was added and further stirring was continued for 2 hrs. The reaction solution to which was added water was extracted with chloroform, washed with diluted hydrochloric acid and 10% sodium carbonate solution and dried over sodium sulfate. The crude product was purified by column chromatography on silica gel. Eluates with 20% ethyl acetate/chloroform afforded 0.88 g of monoglyoxylamide (Y=H) and eluates with 50% ethyl acetate/chloroform afforded 2.25 g of diglyoxylamide

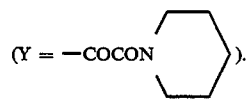

(Y = —COCON⟨piperidine⟩).

(2) Diglyoxylamide (2.25 g) and lithium aluminum hydride (1.0 g) were added to anhydrous THF and the mixture was heated at reflux for 5 hrs. After ice-cooling, unreacted lithium aluminum hydride was decomposed with 10% aqueous NaOH solution and filtered. Evaporation of the solvent gave 2.0 g of the title compound as a solid, m.p. 79°–83° C.

PMR (CDCl₃, δ) 1.25–1.95(20H; m), 2.40–3.00(24H, m), 7.00–7.17 (4H, m), 7.20–7.32(2H, m), 7.45–7.56(2H, m), 8.46(2H, brs)

MASS(EI) 538(M+), 453, 440, 98(100)

EXAMPLE 2

3-(2-Piperidinoethyl)-2,2′-hexamethylenediindole

Monoglyoxylamide (0.88 g) obtained in Example 1 (1) was reacted in a similar manner to that mentioned in Example 1(2). The crude product was purified by column chromatography on silica gel. Eluates with 10% ethanol/chloroform afforded 0.30 g of the oily monoamine (title compound).

PMR (CDCl₃, δ) 1.18–1.85(14H; m), 2.40–2.72(10H, m), 2.80–3.02(2H, m), 6.19(1H, s), 6.97–7.25(6H, m), 7.42–7.56(2H, m), 7.85(1H, brs), 8.52(1H, brs)

MASS(EI) 427(M+), 329, 98(100)

EXAMPLE 3

3-(2-Phenethylaminoethyl)-2,2′-tetramethylenediindole

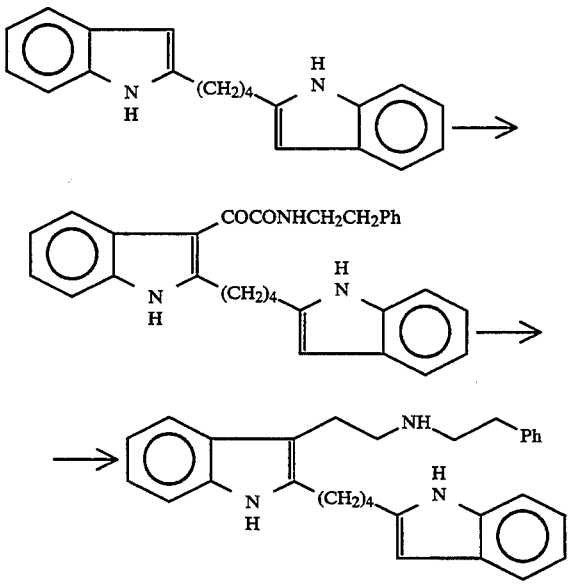

Oxalyl chloride (0.65 ml) was added dropwise under ice-cooling to a THF solution of tetramethylene-2,2′-bisindole (2.0 g). 30 minutes later, 2-phenylethylamine (3.36 g) was added and stirring was continued for 1.5 hrs. The reaction solution to which chloroform was added was washed with diluted hydrochloric acid and brine and then dried over sodium sulfate. The crude product was purified by column chromatography on silica gel. Eluates with chloroform/ethyl acetate (2/1) afforded 0.66 g of glyoxylamide.

To a dioxane solution of glyoxylamide (0.66 g) was added under ice-cooling lithium aluminum hydride (0.66 g) and the mixture was heated at reflux for 5 hrs. Under ice-cooling, unreacted lithium aluminum hydride was decomposed with water and 15% aqueous NaOH solution and filtered. The crude product was purified by column chromatography on silica gel. Eluates with chloroform/methanol (5/1) afforded 0.51 g of the oily title compound.

PMR (CDCl₃, δ) 1.69(5H, brs), 2.6–2.8(6H, m), 2.8–2.95(6H, m), 6.21(1H, s), 7.00–7.30(11H, m), 7.51(2H, d, J=7Hz), 7.67(1H, s), 8.23(1H, s)

MASS(EI) 435(M+), 303, 157, 134, 105(100)

EXAMPLES 4–22

In a similar manner to those mentioned in Examples 1 and 2, the following compounds were prepared from the corresponding amine starting materials.

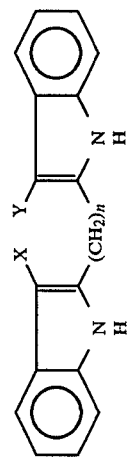

(I)

| Example No. | n | X | Y | Appearance | PMR(CDCl₃, δ), MASS(EI) |
|---|---|---|---|---|---|
| 4 | 8 | —CH₂CH₂N(piperidinyl) | H | Oily | 1.25–1.85(18H, m), 2.50–2.80(10H, m), 2.90–2.98(2H, m), 6.21(1H, s), 7.0–7.15(4H, m), 7.52(2H, d, J=8Hz), 7.76(1H, brs), 8.10(1H, brs) 456(M⁺+1), 358, 98(100) |
| 5 | 4 | —CH₂CH₂N(morpholinyl) | H | Oily | 1.70(4H, brs), 2.0–2.38(6H, m), 2.60–2.84(4H, m), 2.80–2.95(2H, m), 3.75(4H, t, J=4Hz), 6.20(1H, s), 7.0–7.20(6H, m), 7.44–7.56(2H, m), 7.62(1H, brs), 7.80 (1H, brs) 401(M⁺), 301, 144, 100(100) |
| 6 | 4 | —CH₂CH₂N(piperidinyl) | H | Oily | 1.45–1.85(10H, m), 2.40–2.60(4H, m), 2.60–3.00(8H, m), 6.20(1H, brs), 7.00–7.40(6H, m), 7.50(2H, d, J=6.3Hz), 7.81 (1H, brs), 8.35(1H, brs) 400(M⁺+1), 156, 130, 99, 42(100) |
| 7 | 4 | H<br>—CH₂CH₂NCH₂Ph | —CH₂CH₂NHCH₂Ph | Oily | 1.52(4H, brs), 2.56(4H, brs), 2.90(8H, s), 3.75(4H, s), 6.95–7.40(16H, m), 7.47(2H, d, J=7.8Hz), 8.16(2H, brs) 555(M⁺), 436, 318(100), 171, 120, 91 |
| 8 | 4 | —CH₂CH₂NHCH₂Ph | H | Oily | 1.5–1.7(5H, m), 2.5–2.7(4H, m), 2.92(4H, m), 3.74(2H, s), 6.18(1H, s), 6.90–7.30(11H, m), 7.40–7.56(2H, m), 7.62(1H, s), 8.05(1H, s) 421(M⁺), 302, 144, 120, 91(100) |
| 9 | 4 | —CH₂CH₂N(tetrahydroisoquinolinyl) | H | Oily | 1.55–1.74(4H, m), 2.50–2.86(12H, m), 2.86–3.00(8H, m), 3.70(4H, s), 6.21(1H, s), 2.86–7.49–7.60(2H, m), 7.64–7.74(2H, s), 6.85–7.20(14H, m), 606(M⁺), 462, 146(100) |
| 10 | 4 | —CH₂CH₂N(tetrahydroisoquinolinyl) | H | Oily | 1.75(4H, m), 2.6–2.86(8H, m), 2.86–3.20(4H, m), 3.74(2H, s), 6.21(1H, s), 6.90–7.30(10H, m), 7.44–7.60(2H, m), 7.70(1H, s), 7.81(1H, brs) 448(M⁺+1), 146(100) |

-continued (I)

[Structure: bis-indole with X-(CH₂)ₙ-Y substituents on the indole nitrogens]

| Example No. | n | X | Y | Appearance | PMR(CDCl₃, δ), MASS(EI) |
|---|---|---|---|---|---|
| 11 | 4 | -CH₂CH₂N(pyrrolidine) | -CH₂CH₂N(pyrrolidine) | Oily | 1.70(4H, m), 1.82(8H, m), 2.5-2.7(12H, m), 2.75(4H, t, J=7Hz), 2.93(4H, m), 7.08(4H, m), 7.18-7.24(2H, m), 7.52(2H, d, J=7Hz), 8.05(2H, brs) 482(M⁺), 398, 170, 85(100) |
| 12 | 4 | -CH₂CH₂N(pyrrolidine) | H | Oily | 1.60-1.75(8H, m), 2.50-2.77(10H, m), 2.96(2H, t, J=8Hz), 6.17(1H, s), 6.96-7.14(4H, m), 7.14-7.30(2H, m), 7.42-7.56(2H, m), 8.11(1H, s), 8.29(1H, s) 385(M⁺), 84(100) |
| 13 | 4 | -CH₂CH₂NHCH₂Ph | -CH₂CH₂NHCH₂Ph | Oily | 1.61(4H, brs), 2.28(2H, brs), 2.68(4H, brs), 2.71(4H, t, J=7Hz), 2.84-2.96(12H, m), 7.04-7.22(16H, m), 7.50(2H, d, J=7Hz), 8.22(2H, s) 581(M⁺−1), 449, 316(100), 134 |
| 14 | 4 | -CH₂CH₂-N(tetrahydroquinoline) | -CH₂CH₂N(pyrrolidine) | Oily | 1.60(4H, brs), 1.85(4H, t, J=6.4Hz), 2.64(4H, s), 2.71(4H, t, J=6.4Hz), 2.96(4H, t, J=7.6Hz), 3.18(4H, t, J=5.6Hz), 3.50(4H, m), 6.52-7.22(14H, m), 7.56(4H, t, J=7.4Hz) 606(M⁺), 473, 327, 146(100) |
| 15 | 4 | -CH₂CH₂N(tetrahydroquinoline) | H | Oily | 1.6-1.8(4H, m), 1.86(2H, quintet, J=6.2Hz), 2.60-2.82(6H, m), 2.97(2H, t, J=7.5Hz), 3.20(2H, t, J=5.2Hz), 3.51(2H, t, J=7.6Hz), 6.21(1H, s), 6.59(1H, t, J=7Hz), 6.71(1H, d, J=8Hz), 6.97(1H, d, J=7Hz), 7.00-7.16(7H, m), 7.18-7.28(2H, m), 7.67(1H, s), 7.72(1H, brs) 448(M⁺+1), 146(100) |
| 16 | 4 | -CH₂CH₂NHCH₂- (indole-linked) | H | Oily | 1.58-1.75(5H, m), 2.52-2.74(4H, m), 2.88-3.02(8H, m), 6.20(1H, s), 6.70(1H, s), 7.04-7.34(8H, m), 7.46-7.56(4H, m), 7.62(1H, s), 7.72(1H, brs), 8.33(1H, brs) 476(M⁺+2), 345, 303, 144(100) |

-continued (I)

| Example No. | n | X | Y | Appearance | PMR(CDCl$_3$, δ), MASS(EI) |
|---|---|---|---|---|---|
| 17 | 4 | —CH$_2$CH$_2$NCH$_2$Ph<br>\|<br>Me | —CH$_2$CH$_2$NCH$_2$Ph<br>\|<br>Me | Oily | 1.58(4H, brs), 2.34(6H, s), 2.59(4H, t, J=8Hz), 2.65(4H, brs), 2.90(4H, t, J=8Hz), 3.56(4H, s), 7.00–7.16(6H, m), 7.20–7.34(10H, m), 7.43 (2H, d, J=7.4Hz), 7.62(2H, brs) 582(M$^+$), 461, 135(100) |
| 18 | 4 | —CH$_2$CH$_2$NCH$_2$Ph<br>\|<br>Me | H | Oily | 1.56–1.74(4H, m), 2.35(3H, s), 2.56–2.64 (2H, m), 2.64–2.74(4H, m), 2.86–2.94(2H, m), 3.58(2H, s), 6.20(1H, s), 7.0–7.34(11H, m), 7.43(1H, d, J=7Hz), 7.51(1H, d, J=7Hz), 7.59 (1H, brs), 7.83(1H, brs) 435(M$^+$), 170, 135(100), 92 |
| 19 | 4 | —CH$_2$CH$_2$NH(CH$_2$)$_3$Ph | —CH$_2$CH$_2$NH(CH$_2$)$_3$Ph | Oily | 1.68(4H, brs), 1.74–2.0(6H, m), 2.55(4H, t, J=7Hz), 2.62(4H, t, J=7Hz), 2.64–2.76(4H, m), 2.82–2.95 (8H, m) 610(M$^+$), 288, 144(100) |
| 20 | 4 | —CH$_2$CH$_2$NH(CH$_2$)$_3$Ph | H | Oily | 1.58–1.74(4H, m), 1.77(quintet, 2H, J=7Hz), 2.26(1H, brs), 2.53(2H, t, J=7Hz), 2.60(2H, t, J=7Hz), 2.88(2H, d, J=6Hz), 2.92(2H, d, J=6Hz), 6.19(1H, s), 7.00–7.30(11H, m), 7.50(2H, d, J=7Hz), 7.74(1H, brs), 8.39(1H, brs) 450(M$^+$), 303, 148, 91, 44(100) |
| 21 | 4 | —CH$_2$CH$_2$NH(CH$_2$)$_4$Ph | —CH$_2$CH$_2$NH(CH$_2$)$_4$Ph | Oily | 1.40–1.62(8H, m), 1.68(4H, brs), 1.78(2H, brs), 2.54(4H, t, J=7Hz), 2.61(4H, t, J=7Hz), 2.70(4H, brs), 2.89(8H, brs), 7.00–7.30(16H, m), 7.52(2H, d, J=7Hz), 8.34(2H, s) 639(M$^+$+1), 478, 317, 168, 91, 23(100) |
| 22 | 4 | —CH$_2$CH$_2$NH(CH$_2$)$_4$Ph | H | Oily | 1.40–1.64(4H, m), 1.64–1.76(5H, m), 2.55 (2H, t, J=7Hz), 2.60(2H, t, J=7Hz), 2.66–2.76 (4H, m), 2.89(4H, s), 6.19(1H, s), 7.02–7.28 (11H, m), 7.52(2H, m), 7.70(1H, brs), 8.30(1H, brs) 463(M$^+$), 302, 162, 91(100) |

EXAMPLE 23

3,3'-Di(2-(2-pyridyl)ethyl)-2,2'-tetramethylenediindole

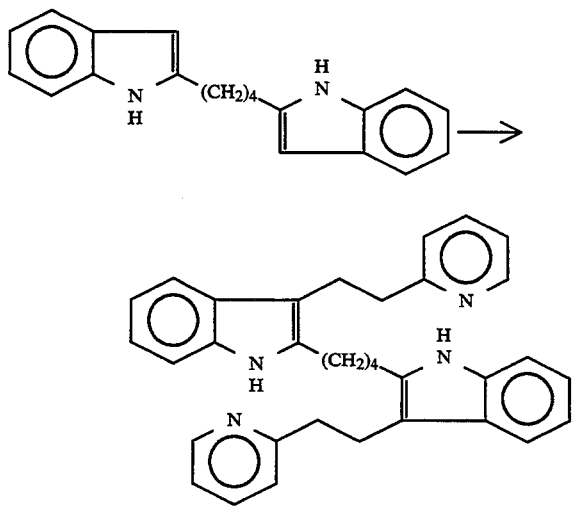

Tetramethylene-2,2'-bisindole (1.11 g) and 2-vinylpyridine (0.81 g) were added to acetic acid and the mixture was heated at reflux for 8 hrs. Acetic acid was evaporated and chloroform was added to the residue, which was washed with 10% aqueous NaOH solution. Such residue was dried over sodium sulfate and the solvent was evaporated. The crude product was purified by column chromatography on silica gel. Eluates with ethyl acetate afforded 1.39 g of the oily title compound.

PMR (CDCl$_3$, δ) 1.47–2.08(4H, m), 2.48–2.62(4H, m), 3.11 (8H, s), 6.95–7.22(10H, m), 7.43–7.58(4H, m), 8.50–8.60(4H,)

MASS(EI) 500(M$^+$+2), 499(M$^+$+1), 407, 219

Further, the following illustrates the H$^+$/K$^+$ ATPase inhibitory activity assay and pharmaceutical preparations of the present compounds.

H$^+$/K$^+$ATPase Inhibitory Activity Assay

The inhibitory activity was determined in the following manner using H$^+$/K$^+$ATPase prepared from the stomach of pig.

H$^+$/K$^+$ATPase dilute solution (100 μl, 50 μg as protein) was added to PIPES-tris (pH 6.2) buffer solution (440 μl) containing 4 mM magnesium chloride and 20 mM potassium chloride. Further, 0.1% ethanol solution of nigericin (5 μl) was added. To the solution was added dimethyl sulfoxide (5 μl) and the mixture was incubated at 37° C. for 30 minutes. Then 10 mM PIPES-tris buffer solution (450 μl) containing 4 mM ATP disodium was added to initiate the reaction. 30 minutes later, 50% trichloroacetic acid (1 ml) was added to cease the reaction. The amount of phosphorus released in this reaction was determined by a color development determination at 800 nm according to D. LeBel, et al. method (Anal. Biochem. 85, 86–89), 1978), at which the reading of the absorbance is taken as C1. On the other hand, a similar determination was carried out in the absence of potassium chloride, at which the reading of the absorbance is taken as C2. The inhibitory activity was determined by a similar procedure as in the above reaction, but adding 5 μl of a dimethyl sulfoxide solution containing 1 to 20 mg/ml of the inhibiting substance (test compound), instead of dimethyl sulfoxide. In that case, the readings of the absorbance in the presence and absence of potassium chloride are taken as T1 and T2, respectively.

% Inhibition (I) of the inhibiting substance (test compound) is calculated by the following equation.

$$I = [(C1 - C2) - (T1 - T2)] \times 100/(C1 - C2)$$

| Test Compound | H$^+$/K$^+$ ATPase % Inhibition |
|---|---|
| Example 1 | 5% (20 μg/ml) |
| Example 2 | 84% (10 μg/ml) |
| Example 3 | 97% (10 μg/ml) |
| Example 4 | 91% (10 μg/ml) |
| Example 5 | 68% (20 μg/ml) |
| Example 7 | 76% (20 μg/ml) |
| Example 8 | 100% (20 μg/ml) |
| Example 13 | 74% (5 μg/ml) |
| Example 16 | 71% (5 μg/ml) |
| Example 17 | 38% (5 μg/ml) |
| Example 18 | 100% (10 μg/ml) |
| Example 19 | 98% (10 μg/ml) |

The pharmaceutical preparations of the present compounds are shown below. Pharmaceutical Preparation 1 - Tablets (one tablet)

| | |
|---|---|
| 3,3'-Di(2-phenethylaminoethyl)-2,2'-tetramethylenediindole | 10 mg |
| Lactose | 67 mg |
| Crystalline cellulose | 15 mg |
| Corn starch | 7 mg |
| Magnesium stearate | 1 mg |

Each ingredient was uniformly blended to prepare powders for direct compression. The powders were formulated by a rotary tableting machine into tablets each 6 mm in diameter and weighing 100 mg. Pharmaceutical Preparation 2 - Granules (one divided form)

| | |
|---|---|
| A. 3,3'-Di(2-phenethylaminoethyl)-2,2'-tetramethylenediindole | 10 mg |
| Lactose | 90 mg |
| Corn starch | 50 mg |
| Crystalline cellulose | 50 mg |
| B. Hydroxypropylcellulose | 10 mg |
| Ethanol | 9 mg |

The ingredients of A were uniformly blended and the solution of B was added. The mixture was kneaded and granulated by extrusion granulation. The granules were dried in a drier at 50° C. and then sieved into the grain size between 297 and 1460 μm. 200 mg of the granules were packed into a unit dosage form. Pharmaceutical Preparation 3 - Syrups

| | |
|---|---|
| 3,3'-Di(2-phenethylaminoethyl)-2,2'-tetramethylenediindole | 1.000 g |
| Refined sugar | 30.000 g |
| D-sorbitol 70 W/V% | 25.000 g |
| Ethyl p-hydroxybenzoate | 0.030 g |
| Propyl p-hydroxybenzoate | 0.015 g |
| Flavor | 0.200 g |
| Glycerol | 0.150 g |
| 96% Ethanol | 0.500 g |
| Distilled water | ad lib |

The compound, refined sugar, D-sorbitol, ethyl p-hydroxybenzoate and propyl p-hydroxybenzoate were dissolved in 60 ml of warmed water. After cooling, a solution of flavor dissolved in glycerol and ethanol was added. The whole mixture was diluted with water to balance 100 ml. Pharmaceutical Preparation 4 - Injections

| 3,3'-Di(2-phenethylaminoethyl)-2,2'-tetramethylenediindole | 1 mg |
|---|---|
| Sodium chloride | 10 mg |
| Distilled water | ad lib |

The compound and sodium chloride were dissolved in distilled water to balance 1.0 ml. Pharmaceutical Preparation 5 - Suppositories

| 3,3'-Di(2-phenethylaminoethyl)-2,2'-tetramethylenediindole | 2 g |
|---|---|
| Polyethylene glycol 4000 | 20 g |
| Glycerol | 78 g |

Polyethylene glycol 4000 was added to a solution of the compound in glycerol. The mixture was warmed and poured into a suppository mold and then cooled to give suppositories, each weighing 1.5 g.

What is claimed is:

1. A compound of formula (I)

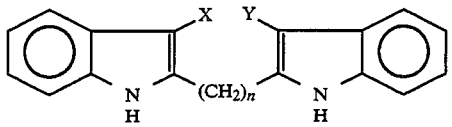

wherein X and Y may be the same or different and each independently represents H or —$CH_2CH_2R$;

R represents pyridyl, morpholino, pyrrolidino, piperidino, 2-(3-indolyl)ethylamino, 1—1, 2, 3, 4-tetrahydroquinolyl, or 2-1,2,3,4-tetrahydroisoquinolyl;

n is an integer of 4 to 8;

with the proviso that X and Y both do not represent H or piperidinoethyl when n is 4, or a pharmaceutically acceptable acid addition salt thereof.

2. A compound of claim 1 wherein X represents —$CH_2CH_2R$, Y represents H or —$CH_2CH_2R$ and R represents pyridyl.

3. A compound of claim 1 wherein X represents —$CH_2CH_2R$ and Y represents H.

4. A compound of claim 1 wherein X represents —$CH_2CH_2R$ and Y represents —$CH_2CH_2R$.

5. A pharmaceutical composition which comprises as an active ingredient an effective amount of a compound of formula (I) as defined in claim 1 or a pharmaceutically acceptable acid addition salt thereof and a pharmaceutically acceptable carrier.

* * * * *